(12) United States Patent
Colquhoun

(10) Patent No.: US 8,065,907 B2
(45) Date of Patent: Nov. 29, 2011

(54) APPARATUS AND METHOD FOR CONTINUOUS MEASUREMENT OF A PHYSICAL PROPERTY OF A DRILLING FLUID

(76) Inventor: Ross Colquhoun, Aberdeen (GB)

( * ) Notice: Subject to any disclaimer, the term of this patent is extended or adjusted under 35 U.S.C. 154(b) by 795 days.

(21) Appl. No.: 12/067,482

(22) PCT Filed: Sep. 19, 2006

(86) PCT No.: PCT/GB2006/003446
§ 371 (c)(1),
(2), (4) Date: Jul. 11, 2008

(87) PCT Pub. No.: WO2007/034152
PCT Pub. Date: Mar. 29, 2007

(65) Prior Publication Data
US 2008/0283294 A1    Nov. 20, 2008

(30) Foreign Application Priority Data
Sep. 20, 2005 (GB) .................................. 0519119.2

(51) Int. Cl.
*G01N 29/00* (2006.01)
(52) U.S. Cl. ..................................................... 73/64.53
(58) Field of Classification Search .................. 73/64.53
See application file for complete search history.

(56) References Cited

U.S. PATENT DOCUMENTS

| | | | | |
|---|---|---|---|---|
| 2,290,179 | A * | 7/1942 | Hayward | 73/152.21 |
| 6,474,143 | B1 * | 11/2002 | Herod | 73/54.01 |
| 6,705,153 | B2 * | 3/2004 | Herod | 73/54.01 |
| 2003/0046986 | A1 * | 3/2003 | Herod | 73/54.01 |
| 2005/0182566 | A1 | 8/2005 | DiFoggio | |
| 2006/0131994 | A1 | 6/2006 | D'Angelico et al. | |

FOREIGN PATENT DOCUMENTS

| | | |
|---|---|---|
| GB | 2 401 944 | 5/2003 |
| WO | WO 01/67098 | 9/2001 |
| WO | WO 2007/034152 | 3/2007 |

* cited by examiner

*Primary Examiner* — John Fitzgerald
(74) *Attorney, Agent, or Firm* — Taft Stettinius & Hollister LLP

(57) ABSTRACT

A testing apparatus comprising a chamber having an inlet and an outlet (16); a measuring device, at least a part of which is provided within the chamber; where the inlet is arranged to direct fluid onto the part of the measuring device within the chamber in order to clean the measuring device during start up. Thus the density or viscosity of drilling mud may be continuously monitored. Some exemplary embodiments include an outlet valve such as a ball valve with a bore defined therein. The bore allows fluid to flow therethrough even in a valve "closed" position and generates the preferred back pressure whilst minimizing the risk that the valve will block. A pressure activated drain valve may also be provided to substantially empty the chamber when not in use.

18 Claims, 6 Drawing Sheets

APPARATUS AND METHOD FOR CONTINUOUS MEASUREMENT OF A PHYSICAL PROPERTY OF A DRILLING FLUID

FIELD OF THE INVENTION

This invention relates to an apparatus and method for generally continuous measurement of a physical property of a drilling fluid. In particular the physical property may be density and/or viscosity.

RELATED ART

To ensure the safe and efficient operation of downhole drilling in drilling rigs or work-over rigs, a fluid generally referred to as a drilling fluid or simply mud or drilling mud is circulated into and out of the borehole being drilled or a borehole which has already been drilled. The drilling fluid is designed to match the chemical and physical environment of the particular well or type of well being drilled or which has already been drilled. In the well, a column of fluid is formed that creates a positive hydrostatic pressure within the wellbore to allow wells to he drilled and/or repaired safely and efficiently.

Generally the drilling fluid is pumped into and out of the well by a fluid pump or mud pump through a drill string and back up out through an annulus (formed between the drill string and a circumference of the well) of the well where the drilling fluid is deposited into a system of surface tanks, shale shakers, solids control equipment, filters etc, before being re-circulated if required for use downhole.

As the fluid is circulated within the wellbore, materials such as brine, silt and rock are removed from the wellbore to the surface by the circulating fluid. The inclusion of such materials can have a detrimental effect on desired properties, such as the viscosity and density, of the drilling fluid. To ensure the desired properties of the drilling fluid are maintained within operational parameters, measurements of these properties are made at regular intervals by on-site personnel. The density of the drilling fluid may be determined for example by using a fluid balance instrument, and viscosity may be checked using a Marsh Funnel. The measurement of the density and viscosity of a drilling fluid are generally made every half-hour or so and the results are generally considered to be representative of all the drilling fluid being circulated within the system at that particular time. However, the physical and chemical properties of the drilling fluid may vary considerably over a given period of time between each batch test of viscosity and/or density of the drilling fluid. Such variances are not desirable, particularly where the viscosity and/or density deviate from operationally acceptable parameters. Other more thorough and time consuming checks (often referred to as mud tests or fluid checks) on the various desired properties of the drilling fluid are generally made to complement the regular batch testing of for example, the density and viscosity of a drilling fluid. Again, however, such testing is on a batch-by-batch basis and repeated only over time periods of at least every few hours or so. Such fluid test/checks require the attention of skilled personnel for relatively long periods of time, and although the results of the fluid tests/checks are of particular importance to the continuing safe and efficient operation of the drilling operation, the results are generally only relevant to the particular batch of drilling fluid which has been checked, and cannot be viewed as being representative of the drilling fluid as a whole between such fluid tests/checks.

It will of course be appreciated that there are a number of physical properties of a drilling fluid which are required to be checked more or less frequently, however, the inventor has found that in order to ensure the safe and efficient operation of a drilling device using a said drilling fluid then it is highly desirable to more or less continuously monitor the viscosity and density of the drilling fluid as it is being used as these characteristics are particularly critical to the efficiency of the fluid. To tackle this problem, British patent application number 2,401,944 (the disclosure of which is incorporated herein by reference) provides an apparatus for the continuous measurement of such drilling fluid properties such as density and viscosity.

FIG. 1 of the present application shows a known system comprising a drilling fluid inlet 106, a drilling fluid chamber 105, a flow meter 115, a valve 107 leading to a drilling fluid outlet 116, a detector 111 comprising forks or tines 102 which extend into the chamber 105 and contact drilling fluid in use. The detector 111 can thus determine the viscosity, density or other physical properties of the drilling fluid continuously.

A problem with the apparatus shown in FIG. 1 is that mud within the drilling fluid tends to gather on the inner walls of the chamber 105 which affects the accuracy of the readings taken by the detector 111 and the immersed forks 102.

Introduction to the Invention:

According to a first aspect of the present invention, there is provided a testing apparatus comprising:
  a chamber having an inlet and an outlet;
  a measuring device, at least a part of which is provided within said chamber;
  wherein the inlet is arranged to direct fluid onto said part of the measuring device within the chamber.

Preferably the distance between the inlet and the said part of the measuring device is at least 10 cm, preferably at least 20 cm, more preferably at least 30 cm.

Preferably the distance between the inlet and the said part of the measuring device is at most 100 cm, preferably at most 80 cm, more preferably at most 60 cm.

Preferably the inlet comprises an inner tube which extends into said chamber such that an annulus is formed between the inner tube and the chamber.

The diameter of the chamber may be at least 3", preferably at least 4", preferably at least 5", optionally over 6".

Thus according to a second aspect of the present invention, there is provided a testing apparatus comprising a:
  chamber having an inlet and an outlet;
  a measuring device, at least a part of which is provided within said chamber;
  wherein the chamber has a diameter of at least 3".

The diameter of the chamber is preferably at least 4", preferably at least 5", optionally over 6".

Preferably the chamber comprises a drain valve.

Preferably the drain valve is activated by a pressure sensing apparatus. More preferably the drain valve is opened when there is a relative drop in pressure and closed when there is a relative increase in pressure. Typically the increased pressure is indicative of liquid substantially being provided within a chamber and the decrease in pressure is indicative of air or another gas being substantially provided within the chamber.

Preferably the diameter of the outlet is smaller than the diameter of the inlet. This provides the preferred back pressure to system in use.

Preferably in use, the outlet is positioned above the inlet.

Preferably, an outlet valve such as a ball valve, may be provided at the outlet.

Optionally at least one further valve may be provided preferably upstream of said outlet valve and preferably downstream of said chamber.

The further valve typically comprises an obstruction, such as a ball, moveable from a first position to a second position. The first position may be an open position and the second position may be a partially closed position. The obstruction may have a bore defined therein such that fluid can flow through the bore typically when the valve is in the partially closed position. In a particularly preferred embodiment, the obstruction is a ball of a ball valve, the ball having a bore for fluid to flow through when the ball is in a certain position, typically the second position.

Preferably the cross-sectional size of the bore is smaller than the cross-sectional size of the inlet. Thus in use in the second position, back pressure is preferably created.

The cross-section of the bore within the valve is preferably substantially circular and so is far less prone to blockages compared to, for example, a conventional ball valve partially open (which would open a crescent-shaped flowpath). Moreover the provision of a bore within the obstruction of the valve reduces the on-site user input and expertise required since the valve simply needs to be moved to the partially closed position whereas use of a proportional valve will require judgment by the user to adjust the valve to the right position.

Such a valve may also be used in other applications and other industries instead of the apparatus described in earlier aspects of the present invention.

Thus according to a third aspect of the present invention, there is provided a valve comprising an obstruction, the obstruction having a throughbore therein, the obstruction moveable from a first open position to a second partially closed position.

Preferably the valve according the third aspect of the invention is the valve according to earlier aspects of the invention.

Typically the present invention provides an apparatus and method suitable for use in substantially continuous measurement of a physical property of a drilling fluid during use thereof in a drilling fluid flow circuit of a drilling device.

Typically supply and return conduits are provided and arranged for connection of said inlet and outlet respectively, in use of the apparatus, to said drilling fluid flow circuit for delivering at least part of the drilling fluid flow through said apparatus.

Typically a pump is provided and arranged for providing a controlled flow of the diverted drilling fluid through the apparatus in use thereof.

Typically the physical property of the drilling fluid to be measured is one or both of viscosity and density.

By substantially continuous measurement of a said physical property, individual measurement of said physical property may be sequentially one after the other, with little or no time interval between each said measurement i.e. in near real time. It will of course be appreciated that a time interval between individual measurements can exist and that such a time interval may be varied as required typically from five seconds to thirty minutes between individual measurements.

The flow circuit of drilling fluid typically includes piping, a drill string (where appropriate), an annulus between the drill string and a borehole and any other conduit and apparatus including any reservoirs used to carry or direct drilling fluid in use thereof.

The chamber is typically in the form of an elongate housing having said inlet at one end thereof and said outlet at the other end thereof. The housing may be of any shape and cross-section preferably generally circular, square, rectangular, triangular, oval, regular and irregular, polygonal shapes may also be considered.

Preferably the chamber is in the form of an elongate cylinder having a longitudinal extent between the inlet and outlet thereof.

It will of course be realised that the chamber will be constructed from a material which is capable of withstanding above atmosphere pressures and be more or less robust and resistant to corrosion. Preferred material such as steel, particularly stainless steel (especially for use in hostile environment such as those found on sea based drilling rigs) are suitable for construction of a chamber.

Preferably, the chamber is arranged so that the main fluid flow direction from the inlet and immediately after the outlet are at an angle alpha with respect to each other.

Preferably the angle alpha is from thirty to ninety degrees.

Preferably the main fluid flow direction from the inlet is, in use, substantially vertical.

Preferably the main longitudinal axis of the chamber is disposed at an angle of between 30 and 90 degrees to the horizontal extent. Preferably therefore one of the inlet and outlet is, in use, above the other of the inlet and the outlet. Preferably the outlet is, in use, above the inlet.

Where the chamber is arranged at such an angle relative to the horizontal this has the advantageous effect of minimising the settlement of various solid/semi-solid components such as Baryte (barium sulphate which is used to inter alia increase the density of the drilling fluid) from the drilling fluid and the flow rate of the drilling fluid through the chamber is very low or has stopped altogether. Advantageously this prevents settlement around the measuring device thereby minimising the risk of inaccurate measurements being taken.

The chamber being arranged at an angle relative to the horizontal allows any such solid/semi-solids to move away under the influence of gravity from the inlet towards the outlet (or vice versa) of the chamber and thereby facilitating the removal of relatively free solids/semi-solids which may precipitate or settle in the chamber.

The measuring device is typically provided and arranged for continuous measurement of physical properties such as density and viscosity, preferably both density and viscosity.

The measuring device may be any device suitable for direct and/or indirect continuous measurements of the physical property typically of a said drilling fluid as it passes through the chamber. Where the device is formed and arranged to measure said physical property directly, then preferably the device is arranged to detect the density and/or viscosity of the drilling fluid. More preferably, the device is also arranged to measure the dynamic and kinematic viscosity, and even more preferably to also measure the temperature of the drilling fluid. Desirably, the measuring device is in the form of a viscometer and/or a densitometer.

Preferably the measuring device has a detector or measurement portion in the form of a tuning fork having a pair of parallel tines. The tines are inserted into the interior volume of the chamber and into a flow of the drilling fluid for direct measurement of a said physical property when in contact with the drilling fluid. Indirect measurements of said physical properties of the measuring device may be achieved by forming and positioning the measuring device or at least a detector portion thereof adjacent or against chamber wherein, in use, the measuring device obtains inductive or capacitive measurements of the drilling fluid passing through the chamber and derives or quantifies a said physical property therefrom.

It will of course be appreciated that the measuring device may utilise a combination of both direct and indirect measurements of one or more physical properties of the drilling fluid.

Desirably, the measuring device of the present invention is provided with suitable display and/or recording apparatus so that the measurements of said physical properties can be monitored and/or recorded. Suitably display/recording apparatus include for example data loggers, personal computers, VDU's, printer devices etc. and any other similar device(s) which can be viewed preferably remotely e.g. in a pit room or shaker house of a drilling rig; or viewed when adjacent to the apparatus.

Supply and return conduits for connection of the inlet and outlet to said drilling fluid flows circuit may be in the form of flexible or rigid pipes or hoses which can be connected to the drilling fluid flow circuit by positioning them at the desired point of suction and the desired point of discharge or connected to the drilling fluid flow circuit by suitable connector devices such as screw fittings. Desirably a supply conduit at least is connected to the drilling fluid flow circuit in use at a point thereon to deliver said at least part of the drilling fluid to the apparatus from said point wherein the drilling fluid is representative of the drilling fluid exited a borehole or other area of operation where the drilling fluid is being used.

By connecting supply conduit at least to a said point in a drilling fluid flow circuit a more accurate and precise i.e. a representative measurement of the physical properties of the drilling fluid being used within the drilling fluid flow circuit.

The pressure within the chamber may be varied by the provision of an adjustable flow valve or other suitable throttling means disposed at/or downstream from the outlet of the chamber. In use the adjustable valve can be open or closed incrementally so as to reduce or produce a backpressure within the chamber as a drilling fluid flows therethrough. By providing a backpressure within the chamber, entrained gas (or at least a proportion thereof) is reduced in volume or dissolved into solution with the fluid as a result of the increase in pressure acting thereon. Additionally, or alternatively gases may be prevented from being displaced from the solution by a said backpressure within the chamber. It is desirable to minimise the presence of entrained gases within the drilling fluid as it passes through the apparatus more particularly through the chamber, as the presence of bubbles of gas may lead to spurious measurements of the physical properties of the drilling fluid.

The pump for providing a control flow of said directed drilling fluid through the apparatus may be located upstream or downstream of the chamber. Preferably the pump is located upstream of the chamber i.e. before the inlet of the chamber.

The pump can be of any known type suitable for use in pumping drilling fluids, however, it will be appreciated that it is desirable to provide pumps which are intrinsically safe for use in environments such as oil drilling rigs i.e. pumps which have a negligible or reduced possibility of providing an ignition source for combustible materials e.g. hydrocarbons, gases, liquids which are generally found on oil drilling rigs. Particularly suitable pumps are pneumatically driven diaphragm pumps. Desirably, said pneumatically driven diaphragm pumps are driven by compressed air provided from a compressed air source such as for example a cylinder containing compressed air or a compressor unit.

As will be appreciated drilling fluids will contain large amounts of solid or semi-solid material when the fluid returns to, for example, a drilling rig during a drilling operation. In order to reduce the possibility of damage to the apparatus in use thereof especially to the measuring device and the pump, the apparatus may be provided with one or more filters disposed upstream of the chamber wherein the filters are formed and arranged to remove unwanted and/or semi-solid materials from a said diverted fluid flow passing through the apparatus. Preferably, the filters are directional in that they will allow only a fluid to pass in one direction therethrough. Desirably there is used a Y-type strainer of generally known type and construction.

Desirably, the apparatus is formed and arranged in a compact and portable and robust form, which can be relatively easily transported to and from and on a rig site without the need of heavy lifting equipment. Preferably the apparatus is transportable in a small trailer capable of being towed behind a private or light goods vehicle. Desirably, the display on the apparatus can be mounted so that it can be placed inside the apparatus as a form of protection during transportation to and from the work site and is secured and attached to a cradle within the apparatus and is capable of being repositioned in a display position when transportation to and from the work site is complete.

Desirably, the apparatus is provided with an enclosure that is suitable for operations on a drilling rig in that it is so called explosion proof and has a so called ingress rating sufficiently high to prevent unwanted ingress of water or other fluid such as the water from a pressure washer the aforesaid enclosure to be used as a housing for electrical components such as voltage transformers, printed circuits, safety relays and other components required.

According to a fourth aspect of the present invention, there is provided a method of determining a physical property of a fluid, the method comprising:

providing a chamber having an inlet and an outlet;
providing at least a part of a measuring device in said chamber;
directing the fluid from the inlet onto the measuring device;
intermittently at least, detecting or measuring a physical property of said fluid;
wherein the flow rate of the fluid through said chamber is varied.

Preferably the method according to the third aspect of the invention is used with the apparatus according to the first and/or second aspect of the invention.

Typically the flow rate of fluid through said chamber is varied from a relatively slow rate, at which detection of the physical property can occur, to a relatively high rate, at which cleaning of a part, typically the said part, of the measuring device can occur.

At the slow rate preferably the method operates to substantially continuously measure or detect the physical property of said fluid.

The relatively slow flow rate can be up to 1 $ms^{-1}$, preferably up to 0.5 $ms^{-1}$, preferably up to 0.1 $ms^{-1}$, preferably up to 0.05 $ms^{-1}$. The relatively high flow rate can be more than 3 $ms^{-1}$, preferably more than 6 $ms^{-1}$, more preferably at least 9 $ms^{-1}$, especially around 10 $ms^{-1}$.

Preferably air or another gas is intermittently directed into the chamber. Thus preferably fluid (predominantly liquid) is normally directed into the chamber whilst air is periodically directed into the chamber. Preferably the air being directed through the chamber causes the variation in flow rate of the fluid since at certain times, a portion of fluid will be present downstream when the air is present upstream and conversely, at certain times, a portion of fluid upstream will be present when air is present downstream; at these times the air affects the flow rate of the fluid.

Thus preferably the effect is that air, then mud will be jetted onto the measuring device to clean it followed by fluid at a relatively high rate, which also serves to clean the measurement device. When air is jetted onto the measurement device, typically no measurement is made.

The physical property measured or detected may be converted by a multiplication factor and by adding a constant in order to improve the accuracy of the results provided. Preferably therefore the physical property measured or detected may be used as the value x in the formula y=mx+c wherein y is the refined (more accurate) value of the physical property, m and c being constants. m and c, especially c, may be different for different types of mud.

Preferably m is 0.7-1.0 more preferably 0.85-0.90.

For brine and water based mud, preferably c is 4.10-4.30, especially 4.20-4.23. For oil based mud, preferably c is 4.40-4.60, especially 4.48-4.50.

Alternatively, or preferably additionally, a separate calibration may be performed by occasionally comparing the results obtained according to the present invention compared to a known device for measuring viscosity or density of mud.

Typically supply and return conduits of the apparatus described herein are attached to a drilling fluid flow circuit.

Typically drilling fluid is pumped from the drilling fluid flow circuit to provide a flow of drilling fluid through the chamber.

Typically the device obtains substantially continuous data of a said physical property of the drilling fluid as it passes through the chamber.

Desirably the apparatus is provided with an audio and/or visual alarm to notify operator personnel when a measured physical property falls outwith a pre-defined operational parameter.

Preferably the apparatus of the present invention forms part of an active control system wherein the apparatus is formed and arranged with a control mechanism which adjusts the composition or other physical property of a drilling fluid when the apparatus detects that a physical property should be measured falls outwith pre-defined operational parameters, so that the physical property is brought within said operational parameters.

The apparatus is preferably provided with an additional fluid feed in fluid communication with the chamber wherein the inlet is formed and arranged to provide an additional volume of drilling fluid and/or a flushing fluid such as water to the chamber if required.

BRIEF DESCRIPTION OF THE DRAWINGS:

An embodiment of the present invention will now be described, by way of example only, with reference to the accompanying figures in which.

Figure 1:
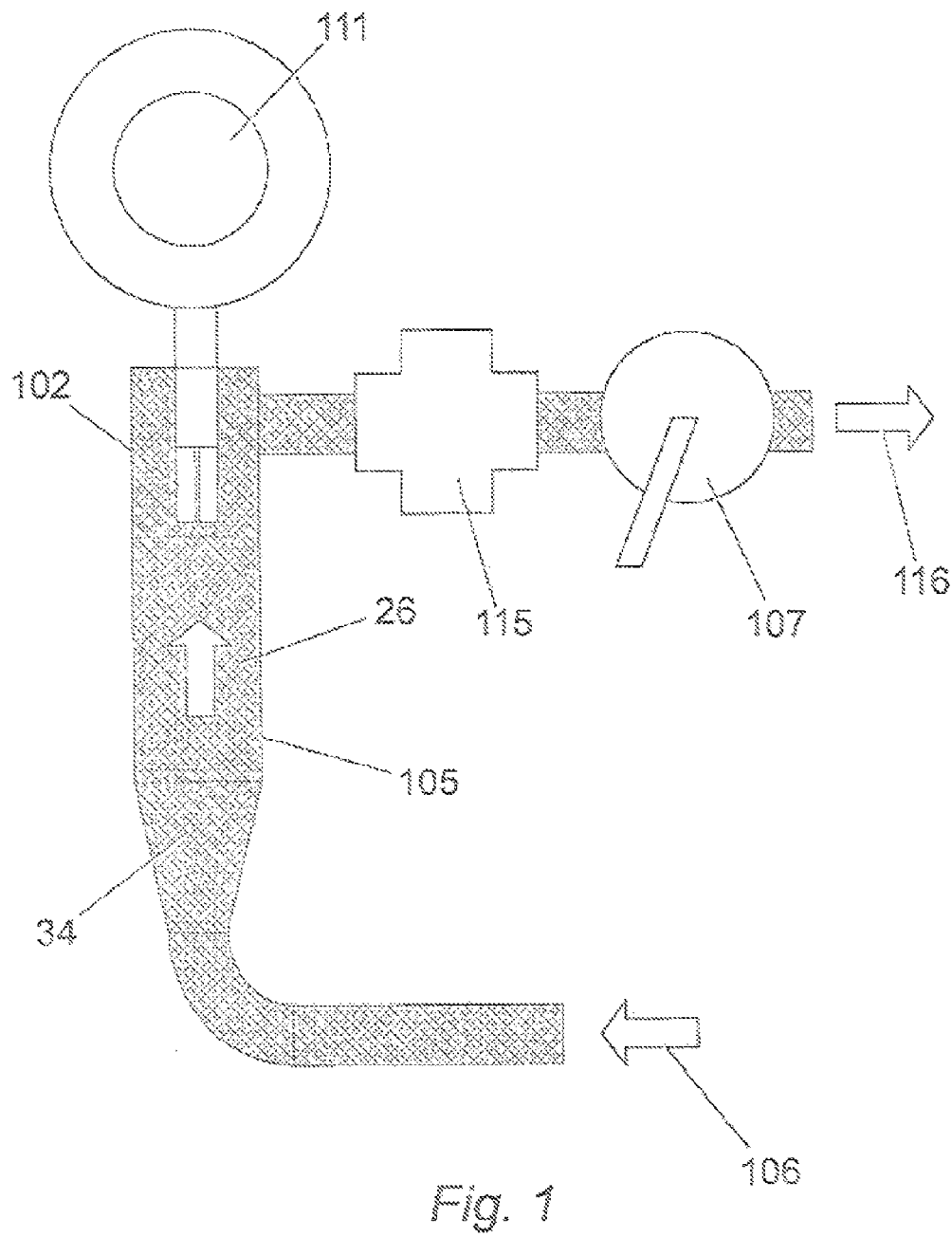
FIG. 1 is a side view of known continuous testing equipment.

DETAILED DESCRIPTION:

The testing apparatus 1 is shown in FIGS. 2-5 and comprises a detection unit 11 with tuning forks or 'tines' 2, the tines 2 being provided within a chamber 5. The chamber 5 has a fluid inlet 6 and a fluid outlet 16 via a ball valve 7. The fluid inlet can have a diameter of around 1" (25.4 mm) and the fluid outlet 16 has a smaller diameter so that pressure may be built up within the chamber 5 during use. The diameter of the fluid outlet 16 can be around 3 mm, typically when taking into account the constriction provided by the valve 7.

As shown in the figures, the main longitudinal axis of the chamber 5 is at an angle 'a' which is 90° to the longitudinal extent, that is the chamber 5 extends upright to encourage some debris to move out of the chamber 5 typically by gravity and not rest within the chamber 5 or on the tines 2.

Figure 3:
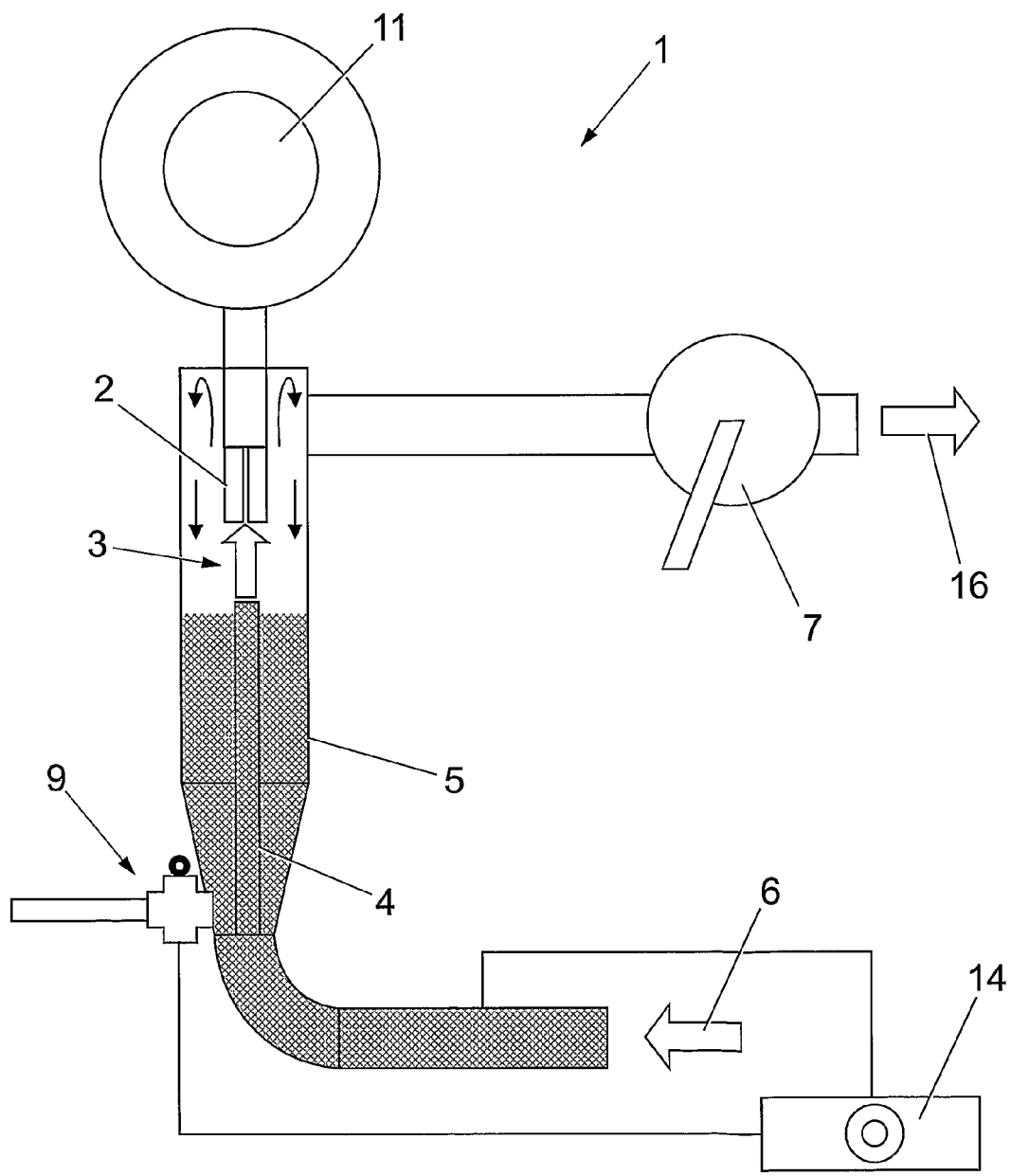
FIG. 3 is a side view of the FIG. 2 testing apparatus also showing a drain valve and activation unit, the chamber of the apparatus approximately half full of drilling fluid.
Figure 4:
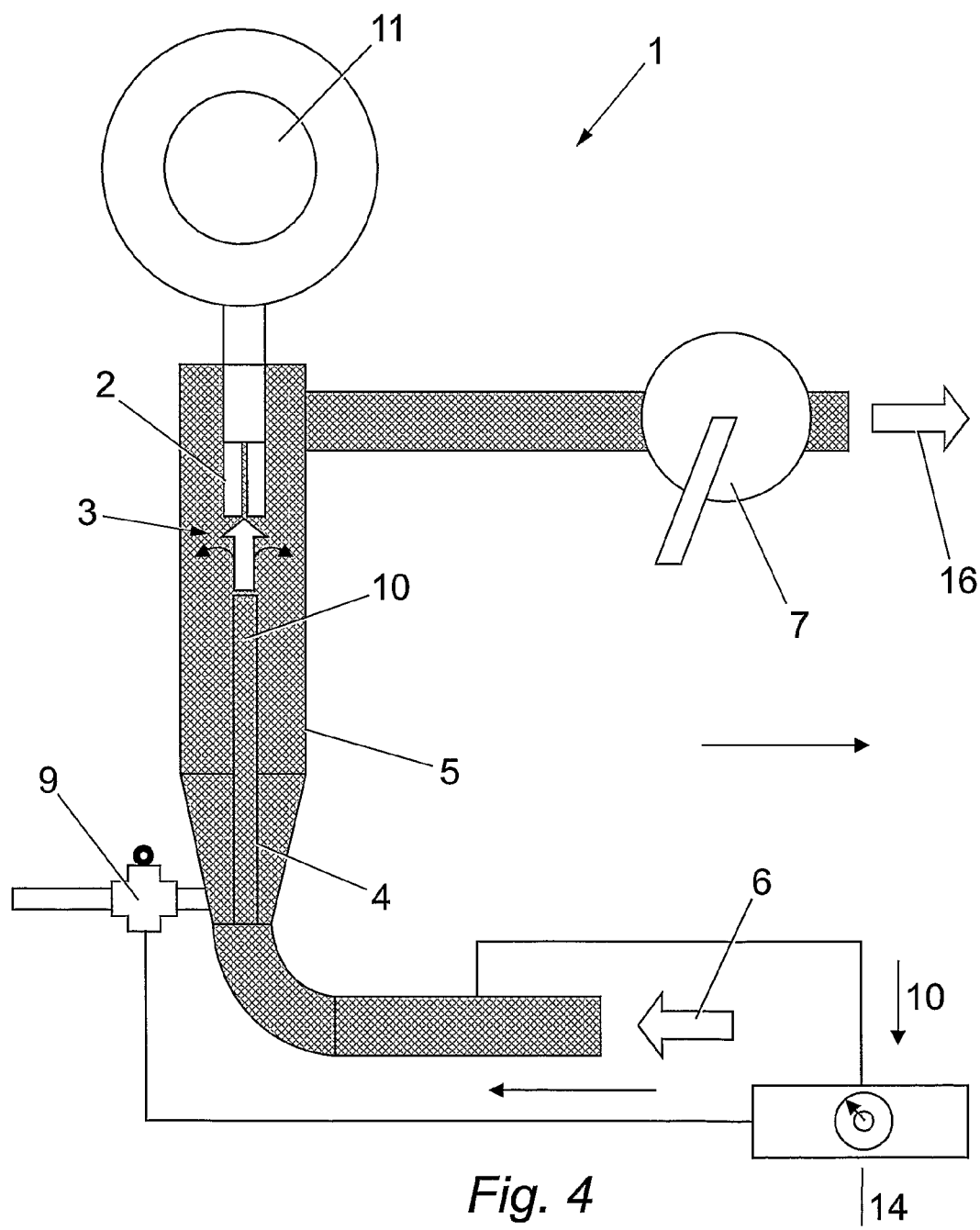
FIG. 4 is a further side view of the FIG. 3 testing apparatus with the chamber full of drilling fluid.
Figure 5:
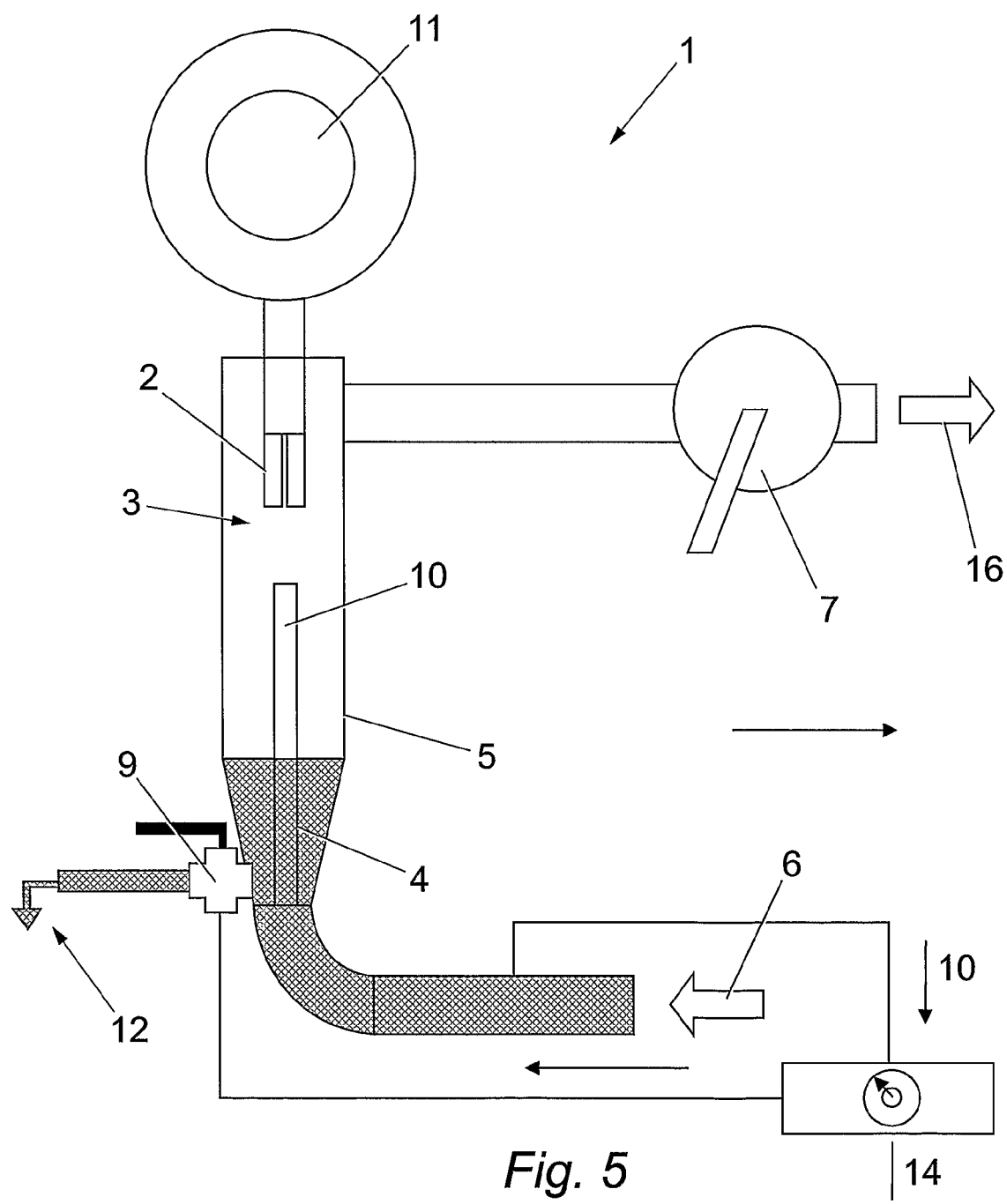
FIG. 5 is a further side view of the FIG. 3 testing apparatus showing discharge of drilling fluid present within the chamber.

As shown in FIGS. 3-5, an activation unit 14 is provided at the fluid inlet 6 which measures the pressure between the fluid inlet 6 and ball valve 7. The activation unit 14 is connected to a drain valve 9 provided in the chamber 5. When said pressure is indicative of fluid, particularly liquid flowing therethrough, the activation unit 14 maintains the drain valve 9 in a closed position. When the pressure falls and so is indicative of air flowing through the ball valve 7, the activation unit 14 opens the drain valve 9 to allow liquid within the chamber 5 to drain therefrom, as will be described in more detail below.

It has surprisingly been found by the inventor of the present invention that increasing the diameter of the chamber 5 reduces the affect of mud deposits on the inner walls of said chamber 5. In this embodiment, the diameter of the chamber 5 is around 150 mm.

Thus embodiments of the present invention benefit in that the effects of the deposits produced on the inner chamber of such a testing apparatus are reduced, particularly when the fluid flowing therethrough is drilling fluid comprising mud.

Without wishing to be bound by any theory, it is thought that sonic signals emitted by the tuning tines 2 do not reach mud deposited on the inner walls of the chamber when a relatively large chamber diameter is used. In known smaller diameter chambers, the sonic signals may have been reflected by the mud on the inside of the chamber, such reflection affecting the accuracy of the results.

As a consequence of the increased diameter of the chamber compared to known testing apparatus, the flow rate is typically reduced which may result in an accumulation of mud or other debris on the tines 2. This can also affect the accuracy of the results produced by the tines 2.

Preferred embodiments of the invention thus comprise a chamber 5 with an inner tubular 4 which communicates with the fluid inlet 6 and directs mud onto the tines 2. In use, this inner tubular 4 functions to clean the tines 2, by intermittently creating jets of mud directed onto the tines 2 which removes debris therefrom, as described in more detail below. The diameter of the inner tubular 4 in this example is around 6 mm.

Figure 2:
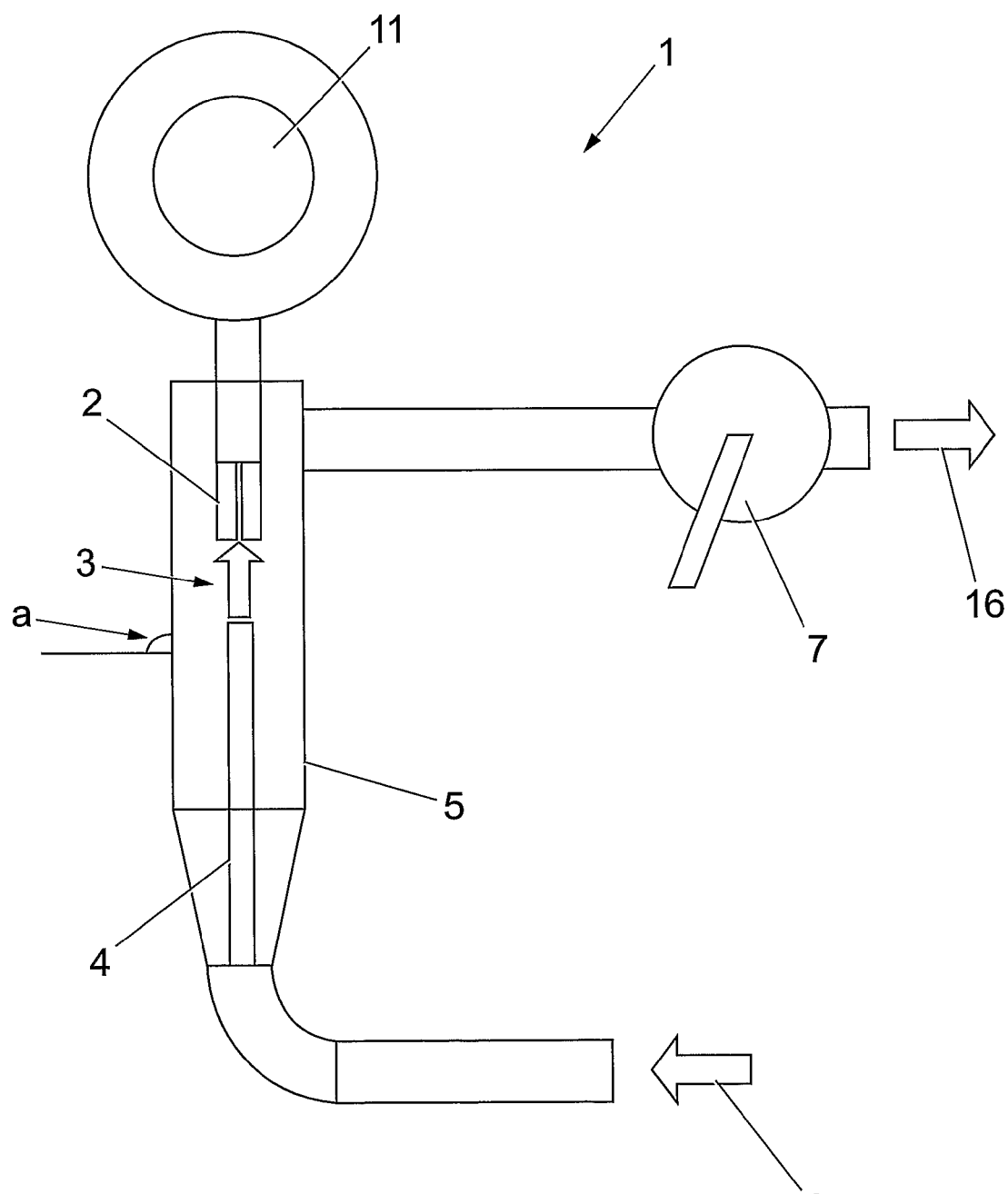
FIG. 2 is a side view of the testing apparatus in accordance with one aspect of the present invention, a chamber of the apparatus without any drilling fluid present.

Thus to operate the testing apparatus 1, air is first pumped through the testing apparatus 1, as shown in FIG. 2 by a pump (not shown). The pump rate is approximately 30 liters per minute. Air proceeds through the fluid inlet 6, through the inner tubular 4 into the chamber 5 and is jetted onto the tines 2. There is insufficient pressure (typically around 1 bar) between inlet 6 and the ball valve 7 to cause the activation unit 14 to close the drain valve 9, which remains open.

Drilling fluid, typically mud, is then fed into the fluid inlet 6 which causes an increase in pressure to around 3 bar and so the activation unit 14 closes the drain valve 9. As shown in FIG. 3, the mud proceeds through the inner tubular 4, is jetted onto the tines 2 then falls into an annulus between the chamber 5 and the inner tubular 4. The flow rate within the inner tubular 4 when it is jetting out of its end 10 onto the tines 2 is relatively quick, that is around 10 m/s. The jetting action typically lasts for a relatively short period of time such as two or three seconds.

In FIG. 4, the mud has reached the ball valve 7 and so the flow rate slows to operational levels, that is around 0.03 m/s. Since the flow rate is reduced, and fluid covers an outlet 10 of the tube 4, mud is no longer jetted onto the tines 2. Therefore, they may now operate to detect the viscosity and density of the fluid within the chamber 5. Such analysis may be continued for a long period of time such as between five minutes to five days, producing important data substantially continuously.

The restriction caused by the ball valve 7 increases the pressure within the chamber 5 to around 6 bar. Gas bubbles which may be present in the mud sample can adversely affect the measurements taken and so the increased pressure helps to mitigate these affects.

FIG. 5 shows the completed sequence, wherein air is fed into the tube 4. This causes the pressure to drop to around 1 bar and causes the activation unit 14 to open the drain valve 9. Mud within the chamber 5 thus escapes from the chamber 5 via the drain valve 9.

The process then starts again by first air jetting onto the tines 2, and then liquid jetting onto the tines 2; both of which help clean the tines 2 so that they provide accurate readings.

In order to introduce the air into the chamber from time to time to create such jetting action, air may be deliberately pumped through the fluid inlet 6. However, in normal operation the mud flow or liquid flow into the testing apparatus is interrupted from time to time and during such operations, the interruptions will cause air to proceed into the fluid inlet 6 and so cause the jetting and cleaning operation as described above.

The detection device 11 and tines 2, may be a Solartron tuning fork, available from Solartron, England, such as models 7827 or 7829.

The tines 2 produce two independent analogue outputs providing values typically in the range of 4-20 mAmps. The first output relates to the density of the mud sample and the second relates to its viscosity.

The output received by the tines 2 are analogue outputs and then converted and displayed digitally. In order to improve the accuracy of the results the reading from the tines may be manipulated depending on the type of mud being analysed, as shown in table 1.

TABLE 1

Exemplary Calibration Constants.

| Mud Type | Graphical response of Density vs mAmps (X = Reading taken. Y = Refined Reading) |
| --- | --- |
| Brine | y = 0.8664x + 4.2193 |
| Water Based Mud | y = 0.8717x + 4.2168 |
| Oil Based Mud | y = 0.8714x + 4.4906 |

Thus if the mud being analysed is oil-based mud and the uncalibrated density reading from the tines is 5 mAmps:

Refined reading=0.8714×5+4.4906

Refined reading=8.8476 mAmp

The refined reading is representative of the density and can be converted into units of density by known means.

Table 1 shows the gradient of the X-Y line to be similar for all mud and/or fluid types but that the different muds have different intersects with the Y axis, particularly the oil-based mud.

In order to even further improve the accuracy of these results, a field calibration of the tines may be performed at the outset of tests and optionally 3, 6, 9 or 12 hours later, depending on the nature of the mud.

The density reading computed above is compared to the reading taken from a commercially available mud balance such as the Halliburton pressure balance, sold under the Trade Mark Truweight™, and a further calculation may be performed to refine the density calculated. An analytical device such as a computer display or digital display, such as the BEKA BA 324D, on the apparatus 1 or a remotely located device may be used to perform such a calculation.

Only one point on the calibration graph may be needed in order to refine the intercept value (that is c in the formula y=mx+c). It has been found that the multiplication factor (m) does not vary significantly following calibration using the values provided in table 1, although a second or further points may always be taken if required. Linearisation software BEKA 324D, may be used to calculate these values.

The tines 2 also produce a separate and unrelated current output which relates to the viscosity of the mud. The same procedure is then conducted for the viscosity.

Thus embodiments of the present invention benefit in that they are able to be calibrated to a high degree of accuracy and will minimise the small variations in response to mAmps by the constantly changing mud properties.

In certain embodiments, a series of ball valves 70 (not shown in FIGS. 2-5) may be provided in the flowpath between the sample chamber 5 and the outlet valve 7.

Figure 6A:
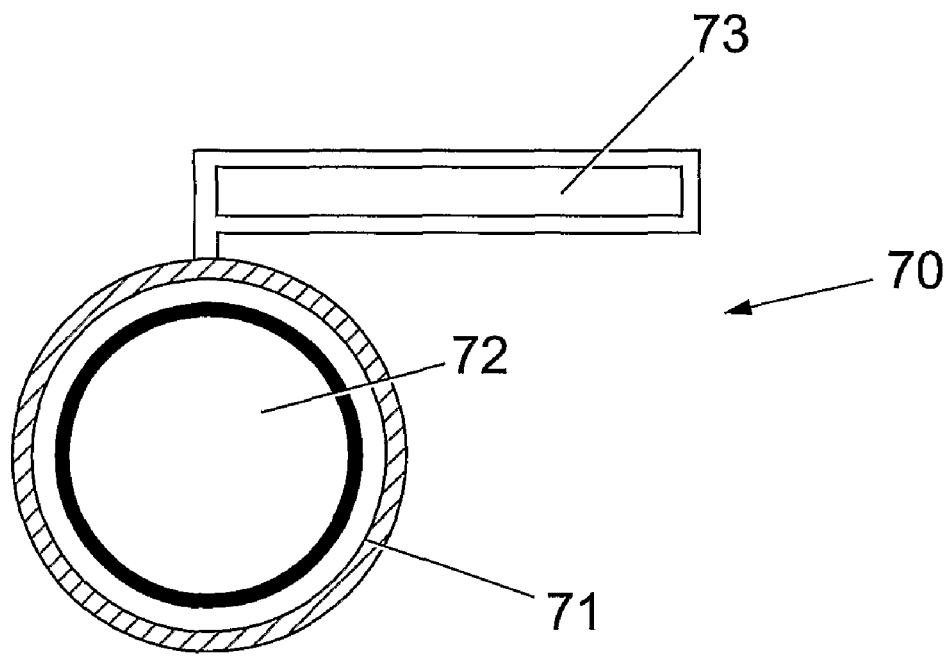
FIG. 6a is a side view of a valve utilized in certain embodiments of the invention in a fully open position; and, FIG. 6b is a side view of the FIG. 6a valve in a partially closed position.
Figure 6B:
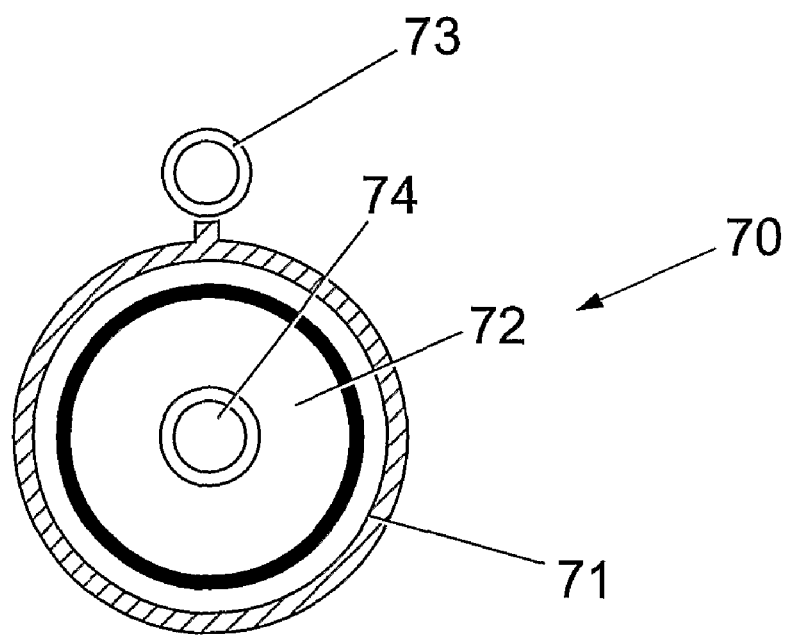

One ball valve 70 is shown in more detail in FIGS. 6a and 6b. The ball valve 70 comprises a housing 71, a ball 72 and a handle 73 operable to rotate the ball 72.

The ball 72 has a hole 74 therein such that when the ball is in a 'closed' positions shown in FIG. 6b, fluid can still pass through the hole 74 in the ball 72 of the ball valve 70. Thus rather than the normal open and closed position provided by a valve, the ball valve 70 has an open 5 position, FIG. 6a, and an almost closed (but slightly open) position, FIG. 6b. This allows an accurate amount of back pressure to be developed within the system for the apparatus to function as described.

The size of the hole can vary from one valve 70 to the next. It is however typically 2-3 mm and can be, for example, 2 mm, 2.5 mm or 3 mm, depending on the viscosity and/or density of the drilling fluid.

Any number of valves 70 may be provided although preferred embodiments have one, two or three valves 70 in series between the sample chamber 5 and the outlet valve 7, again depending on the viscosity and/or density of the drilling fluid.

Since the holes in the balls 72 will normally be the smallest diameter at any point in the flowpath of the apparatus, the holes 74 may block with unwanted solid material. Therefore, 360 degree rotation of the handle 73 is preferred. If the valve 70 is blocked, the handle can be turned 180 degrees to allow the flow of the drilling fluid to unblock the hole 74. Nevertheless, one advantage of such embodiments is that the hole, having a generally circular shaped cross-section, is far less likely to block compared to the use of a proportional ball valve which is opened to provide a flowpath with a crescent shaped cross-section.

The valve 70 may be hydraulically or pneumatically controlled by on-site personnel or remotely by off-site personnel when the apparatus is provided off-shore for example.

Filters (not shown) upstream of the sample chamber 5 are preferred for some embodiments, particularly for embodiments including valves such as the valves 70.

Improvements and modifications may be made without departing from the scope of the invention.

The invention claimed is:

1. A testing apparatus comprising a:
chamber having an inlet and an outlet;
a measuring device, at least a part of which is provided within said chamber;
wherein the inlet comprises an inner tube which extends into said chamber and the inlet is arranged to direct fluid onto said part of the measuring device within the chamber.

2. Apparatus as claimed in claim 1, wherein the chamber has a diameter of at least 3" (7.62 cm).

3. Apparatus as claimed in claim 1, wherein the distance between the inlet and the said part of the measuring device is at most 60 cm.

4. Apparatus as claimed in claim 1, wherein an annulus is formed between the inner tube and the chamber.

5. Apparatus as claimed in claim 1, wherein the measurement device comprises a tuning fork having a pair of tines.

6. Apparatus as claimed in claim 1, wherein the diameter of the outlet is smaller than the diameter of the inlet.

7. Apparatus as claimed in claim 1, wherein in use, fluid flows from the inlet through the chamber to the outlet and said flow is part of a fluid flow circuit of drilling fluid, said circuit further includes piping and an annulus between a drill string and a borehole.

8. Apparatus as claimed in claim 1, wherein a valve is provided at the outlet, the valve comprising an obstruction moveable from a first position to a second position, the first position being an open position and the second position being a partially closed position.

9. Apparatus as claimed in claim 8, wherein the obstruction has a throughbore with a substantially circular cross section defined therein such that fluid can flow through the bore when the valve is in the partially closed position.

10. Apparatus as claimed in claim 1, wherein the chamber comprises a drain valve.

11. Apparatus as claimed in claim 10, wherein the drain valve is controlled by a pressure sensing apparatus.

12. Apparatus as claimed in claim 10, wherein the drain valve is adapted to open when there is a relative drop in pressure and adapted to close when there is a relative increase in pressure.

13. A method of determining a physical property of a fluid, the method comprising:
providing a chamber having an inlet and an outlet, where the inlet comprises an inner tube which extends into said chamber;
providing at least a part of a measuring device in said chamber;
directing the fluid from the inlet onto the measuring device;
intermittently at least, detecting or measuring a physical property of said fluid;
wherein the flow rate of the fluid through said chamber is varied.

14. A method as claimed in claim 13, wherein the physical property of the drilling fluid to be measured is viscosity and/or density.

15. A method as claimed in claim 13, wherein a gas is intermittently directed through the inlet into the chamber.

16. A method as claimed in claim 13, wherein the main fluid flow direction from the inlet is substantially vertical.

17. A method as claimed in claim 13, wherein the flow rate of fluid through said chamber is varied from a relatively slow rate of up to 0.1 ms−1 at which detection of the physical property occurs, to a relatively high rate of at least 3 ms−1 at which cleaning of the said part of the detector occurs.

18. A method as claimed in claim 17, wherein the physical property of said fluid is detected or measured substantially continuously whilst operating at the relatively slow rate.

* * * * *